(12) United States Patent
Ishikawa et al.

(10) Patent No.: US 6,415,184 B1
(45) Date of Patent: Jul. 2, 2002

(54) IMPLANTABLE NEURO-STIMULATOR WITH BALL IMPLANT

(75) Inventors: Akira Ishikawa, Royce City; Nabuo Takeda, Richardson; Suzanne I. Ahn, Dallas, all of TX (US); Samuel S. Ahn, Los Angeles, CA (US); Steven R. Hays, Dallas, TX (US); F. Andrew Gaffney, Nashville, TN (US)

(73) Assignee: Ball Semiconductor, Inc., Allen, TX (US)

( * ) Notice: Subject to any disclaimer, the term of this patent is extended or adjusted under 35 U.S.C. 154(b) by 0 days.

(21) Appl. No.: 09/478,592

(22) Filed: Jan. 6, 2000

Related U.S. Application Data
(60) Provisional application No. 60/115,191, filed on Jan. 6, 1999.

(51) Int. Cl.[7] .................................................. A61N 1/05
(52) U.S. Cl. ........................................ 607/45; 607/116
(58) Field of Search ............................ 607/45, 60, 65, 607/115, 116, 118

(56) References Cited

U.S. PATENT DOCUMENTS

| | | | |
|---|---|---|---|
| 4,832,051 A | * | 5/1989 | Jarvik et al. ............... 607/137 |
| 5,324,316 A | | 6/1994 | Schulman et al. ............ 607/61 |
| 5,397,350 A | * | 3/1995 | Chow et al. .................... 623/4 |
| 5,540,734 A | | 7/1996 | Zabara ......................... 607/46 |

FOREIGN PATENT DOCUMENTS

| | | | |
|---|---|---|---|
| EP | 0 071 131 A2 | 2/1983 | ............ A61N/1/36 |
| WO | WO 97 29802 A | 8/1997 | .......... A61N/1/375 |
| WO | WO 98/43700 | 10/1998 | .......... A61N/1/365 |

* cited by examiner

*Primary Examiner*—Carl Layno
(74) *Attorney, Agent, or Firm*—Howison, Thoma & Arnott, L.L.P.

(57) ABSTRACT

A ball semiconductor for stimulating a mass of nervous system brain tissue for therapeutic purposes. The ball (120) is embedded in a mass of nervous system tissue (215) of a brain. Electrical pulses generated and transmitted to the ball (120) by a remote electrical pulse generator system (140) are picked up by a receiving antenna of the ball (120), and are applied to an electrode pair of the ball (120) to cause the mass of nervous system tissue (215) of the brain located between output pads of the electrode to become stimulated, as therapy for a pathological condition.

38 Claims, 10 Drawing Sheets

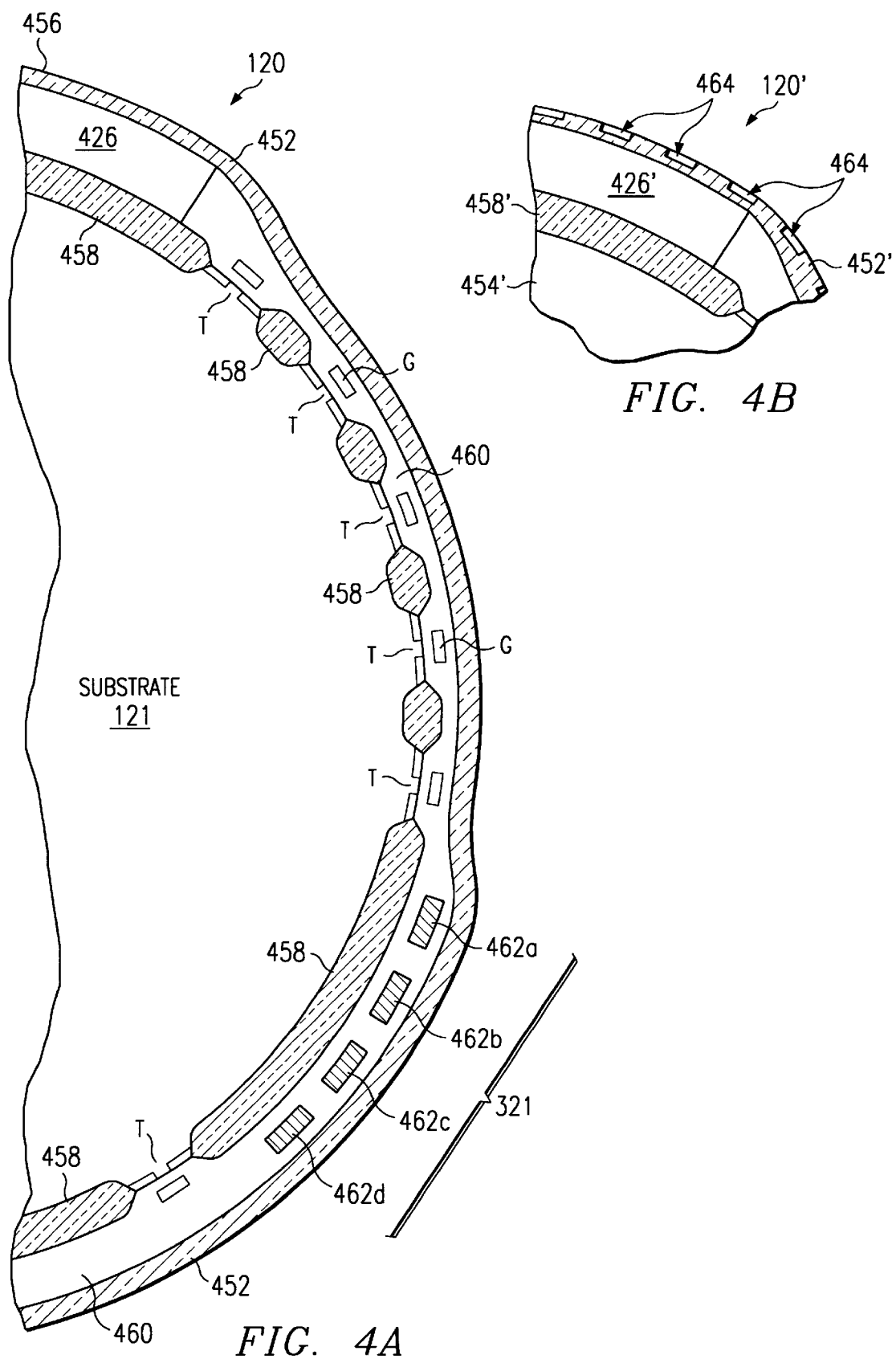

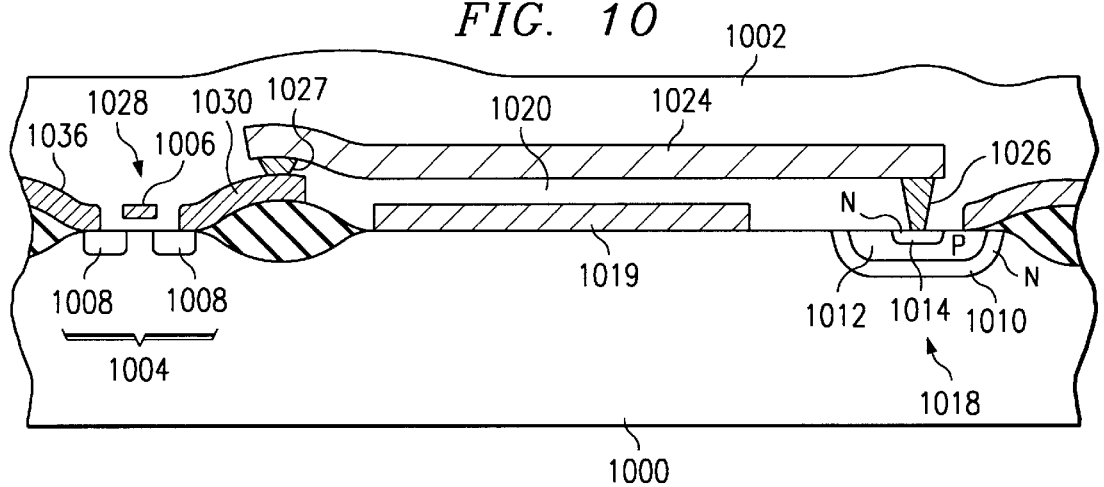
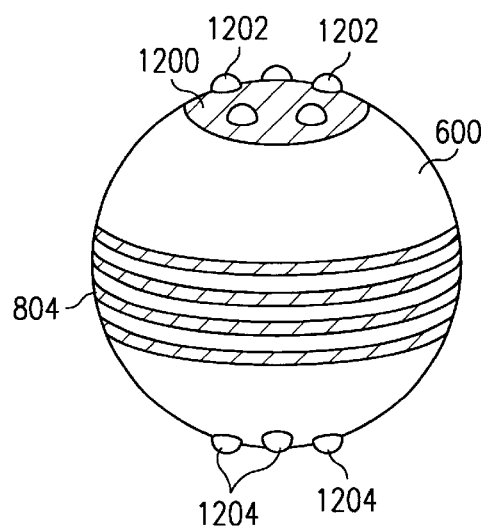
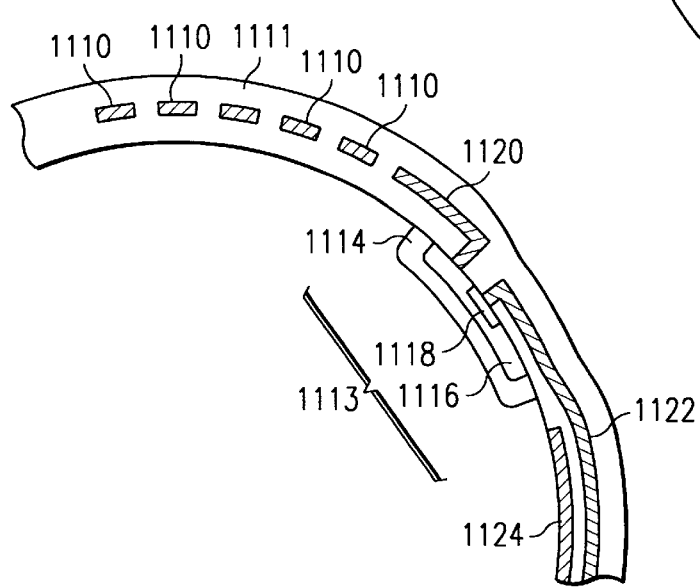

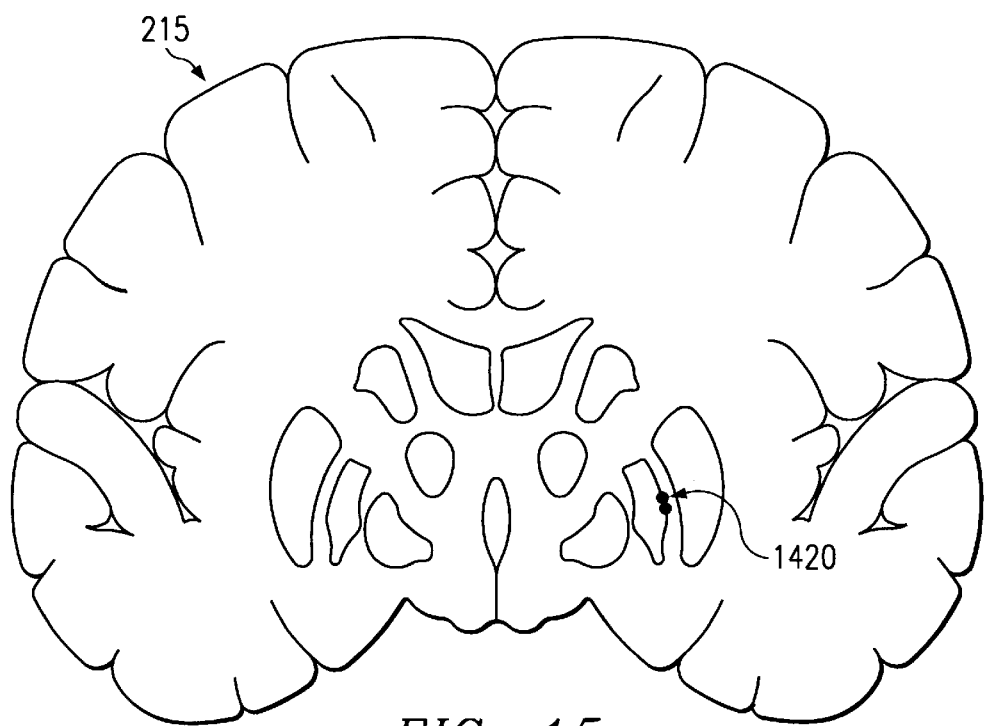
FIG. 15
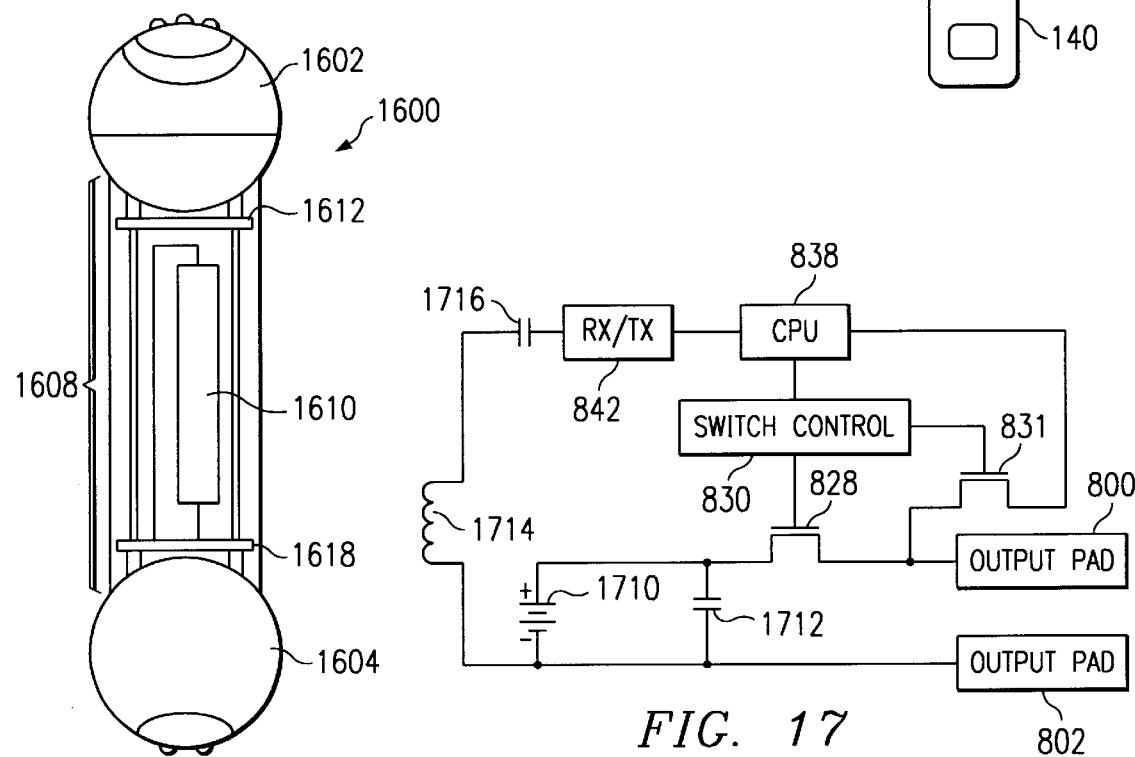
FIG. 16
FIG. 17

IMPLANTABLE NEURO-STIMULATOR WITH BALL IMPLANT

CROSS-REFERENCE TO RELATED APPLICATIONS

This application claims priority under 35 U.S.C. 119(e) from U.S. Provisional Patent Application Ser. No. 60/115,191 filed on Jan. 6, 1999, having the same title as this application.

This application is related to co-pending U.S. patent application Ser. No. 09/323,585 entitled "IMPLANTABLE EPICARDIAL ELECTRODE," filed Jun. 2, 1999; U.S. patent application Ser. No. 09/448,641 entitled "INTRALUMINAL MONITORING SYSTEM," filed Nov. 24, 1999; U.S. patent application Ser. No. 09/448,781 entitled "SPHERICALLY-SHAPED BIOMEDICAL IC," filed Nov. 24, 1999; U.S. patent application Ser. No. 09/448,642 entitled "MINIATURE SPHERICAL-SHAPED SEMICONDUCTOR WITH TRANSDUCER," filed Nov. 24,1999; U.S. patent application Ser. No. 08/478 320, now U.S. Pat. No. 6,295,4 66 entitled "WIRELESS EKG," filed Jan. 6, 2000; U.S. patent application Ser. No. 09/475,819 entitled "INJECTABLE THERMAL BALLS FOR TUMOR ABLATION," filed Dec. 30, 1999; and U.S. Provisional Patent Application Ser. No. 06/163,656 entitled "MEDICALLY IMPLANTED ACCELEROMETER," filed Nov. 3, 1999, each of which is herein incorporated by reference.

TECHNICAL FIELD OF THE INVENTION

This invention is related to an implantable electrode system, and more particularly to an electrode system and method for electrically stimulating neurological tissue.

BACKGROUND OF THE INVENTION

Normal physiologic function of many body tissues and structures depends on the transmission of electrical or electrochemical energy along discrete pathways. Numerous disorders and disease processes arise because of a dysfunction in normal electrical or electrochemical transmission in these tissues.

Various tissues and structures in the body may be artificially stimulated for purposes of enhancing, impeding, or modifying pathological physiologic function. Tissues in the nervous system are especially amenable to such stimulation by virtue of their inherent electrical and electrochemical properties. Physiologic function of nervous system tissue primarily requires the propagation of electrical energy along cell membranes and the release of intracellular chemical packets, which allows intracellular and intercellular communication. The effects of drugs and medications on nervous tissue generally depend on their actions on these processes. However, the use of medications is problematic. Virtually all medications have unwanted side effects, some serious or even fatal. Medications are costly and often require monitoring with periodic laboratory tests. Medication is also often inconvenient to take, especially when more than one daily dose is required. Poor patient compliance with medication is known to be a common reason for medication failure. Even when medications are taken as directed, they may fail to achieve the desired purpose.

Electrodes have been implanted in body tissues to act as modulators of such conditions as epilepsy, movement disorders and chronic pain. The use of such devices has been constrained by several factors, such as difficulty in placement (often requiring dangerous invasive procedures), the inconvenience or impracticality of size, the need for implantable power supplies and the necessity for power supply replacement.

Epilepsy is a pathological condition in which sudden abnormal discharges of electrical activity occur in various sites in the brain. These discharges tend to become hypersynchronous. Abnormal electrical activity may arise from single or multiple foci in the brain. Such activity may affect only circumscribed areas of brain tissue, or it may propagate and affect surrounding brain areas in a more widespread or even generalized fashion. Depending on the location and magnitude of such activity, clinical seizures may occur. Manifestations of seizures include uncontrollable movement of various body parts, abnormal sensations or perceptions or loss or alteration of content of consciousness. In addition to interfering with the normal function of the individual, seizures may result in serious injury or even death. It is known that stimulation of certain brain areas (including but not limited to the basal ganglia and cerebellum) by artificial means may act to inhibit the occurrence or propagation of abnormal electrical activity. Heretofore, such stimulation has been achieved by use of invasive electrodes requiring direct connection to a power source.

A number of pathologic conditions known as movement disorders may arise in the nervous system. These disorders may be caused by trauma, stroke, infection, toxins or unknown factors. This group of disorders includes Parkinson's Disease (primary and secondary forms), Tourette's Syndrome, Huntington's Disease, various tremors (resting, postural and intention types), hemiballismus, various tics and several degenerative diseases. Effects of these conditions include excessive motor activity, inhibition of normal motor activity and abnormalities of muscle tone. These manifestations may range in severity from being simply embarrassing to being incapacitating. Attempts to ameliorate these disorders include the use of medications (which are problematic as discussed above) and various surgical procedures (which are irreversible and pose significant risks). It is known that artificial electrical stimulation of certain brain areas, particularly structures in the basal ganglia or thalamus, may reduce clinical manifestations of these disorders. Such stimulation requires the use of implantable electrode devices coupled with power sources.

Artificial electrical stimulation of the nervous system has also been used to treat conditions of chronic pain. This requires the use of implantable electrode devices connected to power sources.

In addition to the foregoing considerations, it is reasonable to suppose that other disorders of nervous system function (such as behavioral or psychiatric disorders) which have been amenable to pharmacological or surgical treatment might also respond to artificial electrical stimulation of nervous system structures.

Techniques for excitation of neurological tissue are known in the art. In U.S. Pat. No. 5,713,922, by King, entitled "Techniques For Adjusting The Locus Of Excitation Of Neural Tissue In The Spinal Cord Or Brain," issued Feb. 3, 1998, one such technique is described where two anodes and a cathode are implanted into neurological tissue. Hardwired to the electrodes is a fully implanted or partially implanted electrical pulse generator. Electrical pulses from the generator are applied to the electrodes and the signal produced across each anode cathode pair is used to stimulate the neurological tissue of interest. A remotely located programmer allows an attendant to adjust the settings of the electrical pulse generator by radio frequency communication. However, these and other known neurological stimulation techniques are hampered by size, power, and communication constraints, among other things.

SUMMARY OF THE INVENTION

The present invention disclosed and claimed herein comprises, in one aspect thereof, a ball semiconductor system for stimulating a mass of nervous system tissue in a body for therapeutic purposes. The semiconductor ball adaptable to be embedded in the mass of nervous system tissue, and which ball semiconductor comprises a cathode and an anode electrode pair, and a receiver for wirelessly receiving electrical pulses for application to the electrode pair. A remote electrical pulse system communicates with the semiconductor ball and comprises a generator for generating the electrical pulses, and a transmitter for wirelessly transmitting the generated electrical pulses to the receiver of the semiconductor ball. The electrical pulses are applied to the electrode pair to cause the mass of nervous system tissue to become stimulated to therapy a pathological condition.

BRIEF DESCRIPTION OF THE DRAWINGS

For a more complete understanding of the present invention and the advantages thereof, reference is now made to the following description taken in conjunction with the accompanying Drawings in which:

FIG. 4A illustrates a more detailed cross section of the semiconductor structure of the ball;

FIG. 4B illustrates an alternative embodiment of a ball having recesses for reducing tissue adhesion to the ball;

FIG. 10 illustrates a cross-sectional view of the semiconductor device in the form of the spherical IC which has been "planarized" to remove the curvature thereof;

FIG. 11 illustrates a cross-sectional diagram of the surface of the ball illustrating conductive strips which form the inductive element;

FIG. 12 illustrates a perspective view of the ball, wherein the inductive element is illustrated as being strips of conductive material wrapped around the exterior of the ball;

FIG. 15 illustrates an electrode pair defined by the semiconductor balls having been placed in the mass of nervous tissue of the brain to wirelessly receive electrical pulses generated from a remote location by a electrical pulse generator;

FIG. 16 illustrates a side view of an alternate embodiment of a two-ball electrode stimulator having an onboard power source;

FIG. 17 illustrates a schematic block diagram of the stimulator of FIG. 16 having an onboard battery as a power source;

DETAILED DESCRIPTION OF THE INVENTION

The spherical geometry of the semiconductor ball devices disclosed herein offer a number of advantages compared to conventional semiconductor devices having a planar or two-dimensional geometry. By way of illustration, a few of these advantages include the following: a spherical device has a smooth, rounded shape which is easily implanted or injected into a biological medium and which may pass easily through a biological medium if necessary in a particular application. Further, the large surface area of a spherical device relative to its overall dimensions provides for a maximum of surface area devoted to functional regions in contact with the biological medium, such as transducers and other circuitry while maintaining a device of the smallest possible size for ease of passage through a vascular system, implantation, etc. Further, the spherical device permits disposition on a single device of transducers aligned on all three geometric axes for maximum transducer function. Moreover, the rounded, three-dimensional shape of the spherical IC permits an inductor to be wound on the surface thereof which more closely approximates the ideal cylindrical form of an inductor.

Figure 1:
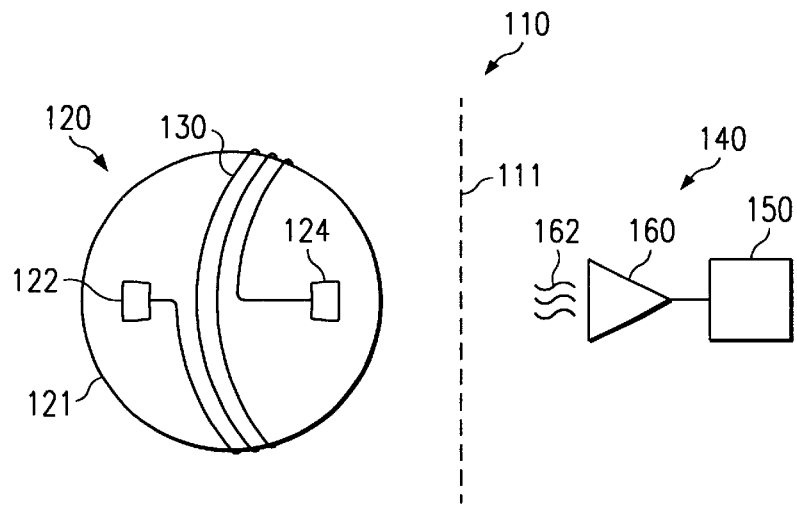
FIG. 1 illustrates a ball semiconductor system for stimulating a mass of nervous system tissue in a body for therapeutic purposes.

Referring now to FIG. 1, there is illustrated a ball semiconductor system for stimulating a mass of nervous system tissue in a body for therapeutic purposes.

The ball semiconductor system 110 comprises a substantially spherical ball semiconductor 120 (hereinafter called a "ball") which is implanted in a body and a remote electrical pulse generator system 140 positioned outside of the body, as demarcated by a line 111 designating the surface of the body. In this embodiment, the ball 120 comprises a cathode 122 and an anode 124 fabricated on a substrate 121, and which together form an electrode pair, and an inductance 130 for wirelessly receiving electrical pulses for application to the electrode pair. More complex ball embodiments are disclosed hereinbelow which comprise onboard intelligence for more precise control and feedback of ball 120 operations during the medical procedure. The construction of such ball 120 is disclosed in commonly-assigned U.S. patent application Ser. No. 5,955,776 entitled "Spherical Shaped Semiconductor Integrated Circuit," which issued Sep. 21, 1999, which is incorporated herein by reference.

The electrical pulse generator system 140 comprises a processor 150 (or control logic) which controls a pulse generator 160 for generating electrical pulses 162, and an antenna (not shown) for wirelessly transmitting the generated electrical pulses 162 to the receiving inductance coil 130 (or antenna) of the ball 120. Preferably, the electrical pulses 162 are transmitted at a radio frequency (RF) level in accordance with the above-referenced commonly assigned patent application. It will be appreciated that other wireless transmission techniques may also be used. The construction of pulse generators and wireless transmission means are well known in the art. See, for example *ELECTRONIC ENGINEERS' HANDBOOK*, Second Edition, Fink Christianson, McGraw Hill, 1982.

Figure 2:
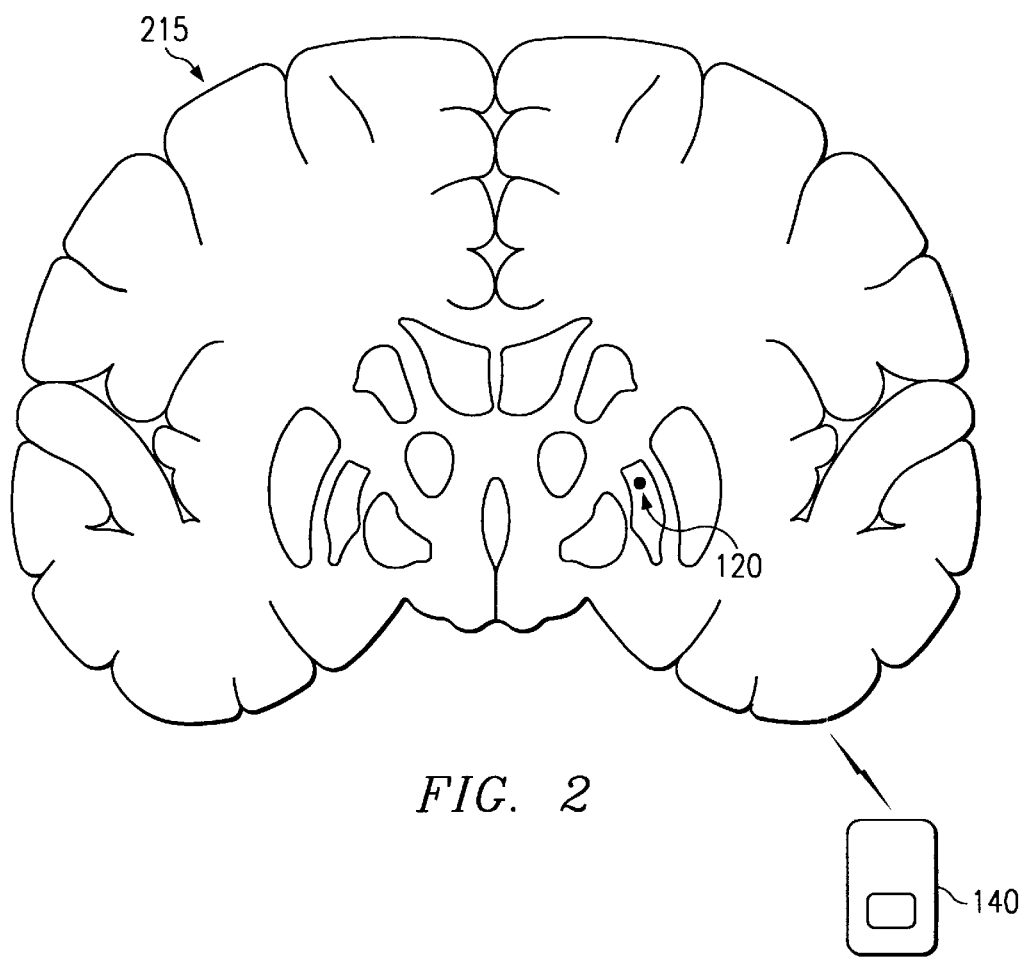
FIG. 2 illustrates the ball embedded in a mass of nervous system tissue of a brain.

Referring now to FIG. 2, there is illustrated the ball 120 embedded in a mass of nervous system tissue 215 of a brain. Electrical pulses 162 generated and transmitted to the ball 120 by the remote electrical pulse generator system 140 are picked up by the receiving antenna 130 of the ball 120, and are applied to the electrode pair defined by the anode 124 and cathode 122 to cause the mass of nervous system tissue 215 of the brain located between output pads of the electrode to become stimulated, as therapy for a pathological condition.

The amount and nature of the electrical stimulation of the tissue 215 depends upon the characteristics of the electrical pulse which is transmitted across the gap separating the two electrodes. For instance, a waveform having a prescribed pulse amplitude and frequency, a variable amplitude and frequency, an impulse profile, one-shot or other signal profile can be used as required to provide the desired therapy. Selecting an appropriate electrical pulse for the appropriate therapy is based upon several criteria, including the therapy desired, the condition of the body and the nerve site being stimulated, the duration of therapy, and other factors in accordance with a protocol that may be established for a particular therapy. Specific electrical pulses useable with this invention are known in the art, such as the pulses described in above-referenced U.S. Pat. No. 5,713,922, which is incorporated herein by reference.

Figure 3:
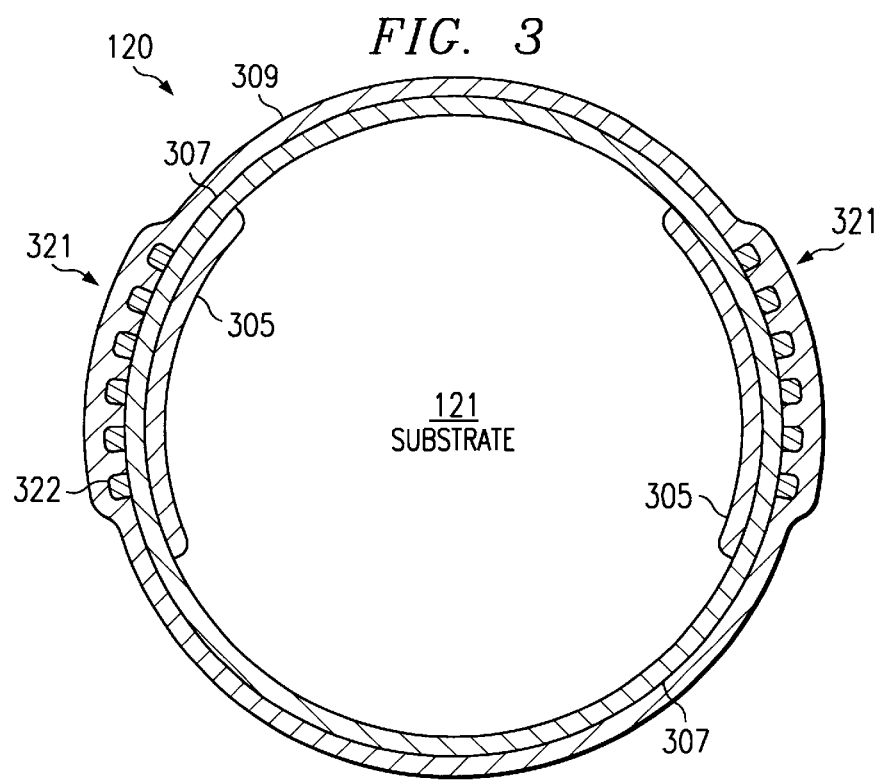
FIG. 3 illustrates a coss section of a transponder ball, preferably comprising a spherical-shaped semiconductor device on which an integrated circuit has been formed.

Referring now to FIG. 3, there is illustrated a coss section of a transponder ball, preferably comprising a spherical-shaped semiconductor device on which an integrated circuit has been formed. Such a spherical-shaped integrated circuit semiconductor device is described in the above-referenced U.S. Pat. No. 5,955,776 entitled "Spherical Shaped Semiconductor Integrated Circuit," which issued Sep. 21, 1999. The ball 120 is built on the substantially spherical semiconductor substrate 121, which may be doped P-type or N-type in accordance with the particular requirements of the fabrication process. Semiconductor circuitry, indicated generally at 305, resides on the substrate 121. Circuitry 305 includes the electrode pair (anode 124 and cathode 122) and the receiving antenna 130, as well as other circuitry necessary for providing the desired stimulative output. The substrate 121 and circuitry 305 are covered with an insulating layer 307 which is preferably formed of silicon dioxide or phosphosilicate glass. The antenna 130 is a coil 321 formed of helically wrapped windings 322 over the insulating shell layer 307. The antenna 130 may be fabricated from a deposited layer of aluminum that is patterned and etched using conventional semiconductor fabrication techniques. The actual number of individual windings 322 of coil 321 may be more or less than the six shown in FIG. 3. The ball 120 is coated with or encapsulated in a coating layer 309 of a biological inert material such as phosphosilicate glass. (Notably, it has also been found that encapsulating the balls in a substantially biologically inert coating allows the semiconductor balls to be biologically friendly.) The coating 309 can withstand potential chemical degradation from the biological medium which it contacts, for example, the acidity of the stomach, to a very low pH level, and it is not subject to the enzymatic actions of the digestive tract. The ball 120 is substantially spherical and preferably about one millimeter in diameter. The very small size of ball 120 enables it to be embedded in surgical or medical tools and apparatus, and injected or implanted in a wide variety of biological tissues.

Referring now to FIG. 4A, there is illustrated a more detailed cross section if the semiconductor structure of the ball 120. The ball 120 is hermetically protected by a thin exterior glass passivation layer 452, which may be phosphosilicate glass. The interior of the ball 120 comprises the semiconductor substrate 121, which may be doped P-type or N-type in accordance with the particular requirements of the fabrication process. Optionally, the substrate 121 maybe connected to a surgical instrument or other metallic device to serve as a ground potential for the ball 120. In an alternative embodiment where a sensor 426 is employed, the sensor 426 has an outer surface 456 that is exposed to the biological medium. The sensor 426 preferably is formed atop a thick dielectric layer 458, which may be a field oxide layer grown on the substrate 121.

A large number of transistors T (many of which are not shown) constitute the circuitry 305 of the ball 120, for example, in an embodiment having onboard power regulation for stabilizing power to onboard electronics (described in greater detail hereinbelow with reference to FIG. 5). Although these transistors T are schematically depicted as MOS transistors, the integrated circuitry 305 of the ball 120 could also use bipolar transistors. The individual transistors T are shown separated by portions of the field oxide 458. Transistor gates G and circuit interconnections (not shown) are embedded in an inter-level dielectric layer 460 and are made using conventional semiconductor fabrication techniques adapted to the spherical surface of the ball 120.

The antenna 130 is shown as a coil 321 having a plurality of separate windings 462a, 462b, 462c and 462d, which may be fabricated from a deposited layer of aluminum (or copper) that is patterned and etched using conventional semiconductor fabrication techniques adapted to the spherical shape of the ball 120. The windings 462a, 462b, 462c and 462d are insulated from each other by portions of the inter-level dielectric layer 460. The actual number of individual windings 462a, 462b, 462c and 462d of the coil 321 may be far greater than the four specific windings shown. The ends of the coil 321 are connected by additional conductors (not shown) to other circuit elements of the ball 120.

Referring now to FIG. 4B, there is illustrated an alternative embodiment of a ball 120' having recesses for reducing tissue adhesion to the ball. The ball 120' includes a substrate 454' on which a thick field oxide 458' has been grown. Overlying the thick field oxide 458' is, for example, a pressure transducer 426' whose outer surface has been modified, in accordance with a disclosed embodiment. The portion of dielectric layer 452' lying over the transducer 426' has recesses 464 formed in its outer surface. These recesses 464 may also extend beyond the edges of the transducer 426' at least so far as the monitor's surfaces may be exposed to the bloodstream.

The purpose of the recesses 464 is to inhibit tissue adhesion to the surfaces of the ball 120' that are exposed to the body tissues. Tissue adhesion is known to occur on the surfaces of implants through the attachment of fibroblasts. This phenomenon is well known and is described in Von Recum et al., "Surface Roughness, Porosity, and Texture as Modifiers of Cellular Adhesion, " *TISSUE ENGINEERING*, Vol. 2, No. 4, 1996 (available from the Dept. of Bioengineering, Clemson University, Clemson, S.C.). The recesses 464 are presently preferred to be about one micron deep, three microns wide, and spaced three microns apart in a checkerboard topography. Such recesses can be fabricated by conventional selective etching techniques adapted to the spherical shape of the ball 120.

Figure 5:
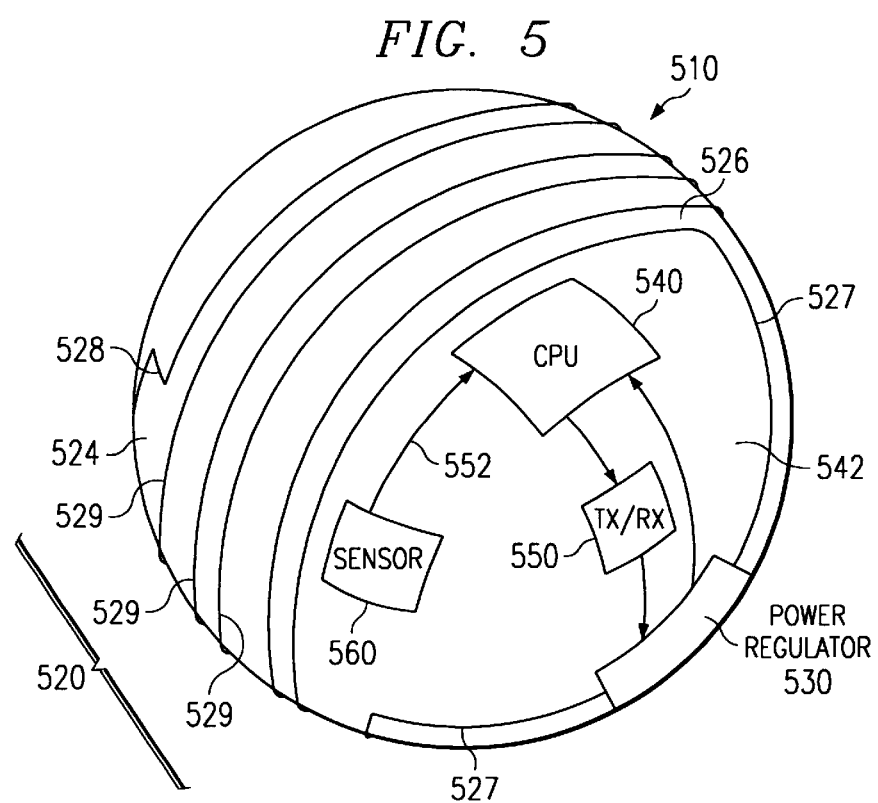
FIG. 5 illustrates one embodiment of a ball having power and sensing capabilities.

Referring now to FIG. 5, there is illustrated one embodiment of a ball 510 having power and sensing capabilities. A power source for the semiconductor ball 510 (similar to ball 120) is provided by an inductance coil 520 which becomes energized by a separate nearby source (not shown) which provides a varying magnetic field for inducing electric energy into the inductance coil 520. The inductance coil 520 is formed of a conductive path or wire 528 which is wound on the surface of a substrate 542 around the semiconductor ball 510, with nonconductive spaces 524 and 526 between windings 529. The inductance coil 520 is coupled with a power regulator 530 via a conductive path 527 which provides a relatively constant DC voltage of about 3 volts to the circuits on the ball 510. (Note that as advances in technology permit, the required voltage levels to power the onboard circuits may be less then the disclosed 3 volts.) An onboard processor 540 connects to the power regulator 530 to obtain power therefrom, and it can be appreciated that the processor 540 could be configured to also route power through from the power regulator 530 to other onboard circuits, such as an RF communication circuit 550 and one or more sensors 560. In any case, the processor 540 connects to both the RF communication circuit 550 and the sensor(s) 560 for monitor and control thereof. The sensor(s) 560 are fabricated on or near the surface of the ball 510 where exposure to a portion of a biological medium in which a parameter is to be sensed by the sensor(s) 560 or affected by an actuator (not shown) is better accommodated. The transducer 560 is coupled to the processor 540 via a line 552.

Alternatively, the ball 510 may be powered by a miniature battery (not shown, but illustrated and discussed in greater detail hereinbelow) which is connected to the ball 510, as well as to clusters of similar balls with different functions, such as a memory. The miniature battery may also have a substantially spherical shape to accommodate a common connection scheme between adjacent balls. Preferably, such battery balls may be an electric double layer condenser formed of such materials as manganese dioxide, lithium, carbon or lithium ion, etc. Since such a battery ball provides a greater capacity energy source than radio frequency energy generated through the inductance coil 520, longer communication distances can be achieved.

The inductance coil 520 has ends (not shown) that are connected by subsurface conductors (not shown) to the other circuit elements on the ball 510. It will be appreciated that the inductance coil 520 may have many more windings 529 than the 5-6 windings actually shown. The signal processor 560 provides an output to the transmitter/receiver 550 that preferably radiates an RF signal to a external receiver (not shown) at another location. Both the remote magnetic field generator and receiver can be included in a common computer-controlled apparatus or central processing unit (CPU) station within proximity of the ball 510, at least when its operation is required.

Figure 6:
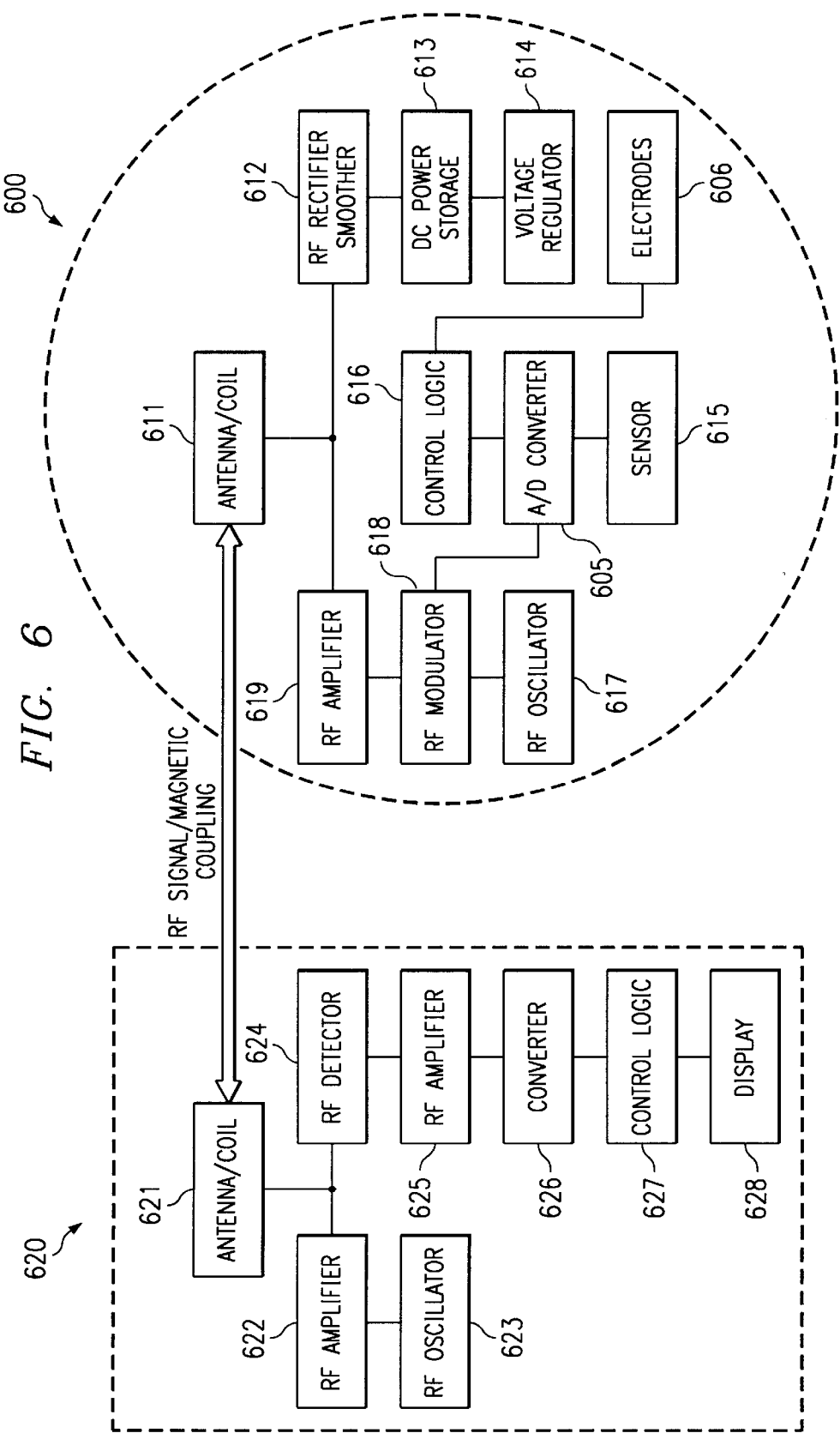
FIG. 6 illustrates an alternative embodiment of a ball and an external monitor and control system.

Referring now to FIG. 6, there is illustrated an alternative embodiment of a ball and an external monitor and control system. A control unit 620 includes an antenna/coil 621 that transmits RF power to an antenna/coil 611 of ball 600 (similar to balls 510 and 120). This coil 621 is tuned for a specific frequency, such that multiple balls can operate in the same free space with no channel contention. Power is transported to the ball 600 either by RF radiation or by magnetic coupling between the external antenna/coil 621 and ball antenna/coil 611. The control unit 620 generates RF power with an RF oscillator 623 coupled to an RF amplifier 621. The RF amplifier 621 is coupled to the control system antenna/coil 621. The RF power received at antenna/coil 611 of ball 600 is rectified and smoothed by an RF rectifier smoother 612 coupled to the ball antenna/coil 611. The RF rectifier smoother 612 converts RF energy to a DC voltage. The DC power is stored in a DC power storage unit 613, which may be a capacitor, a battery, or the combination thereof. The capacitor of the DC power storage unit 613 may be included in the smoothing portion of RF rectifier smoother 612. A voltage regulator 614 is coupled to the DC power storage unit 613. The voltage regulator 614 regulates the DC voltage to provide stable voltage for powering the ball 600 for any condition or distance between monitoring unit 620 and the ball 600. The voltage regulator 614 supplies DC voltage to all circuits of ball 600, in a manner well-known to those skilled in the art.

The ball 600 includes electrodes 606 for stimulating the brain tissue 215, which electrodes 606 connect to a control logic circuit 616 for control thereof. Optionally, the ball 600 includes one or more sensors 615 for measuring the desired quantitative conditions of the physical medium. The output of the sensor 615 is connected to an analog-to-digital (A/D) converter 605 for conversion to a frequency signal. The control logic 616 communicates with the A/D converter 605 for conversion of the measured temperature data. The control logic 616 may be configured to control the activity of all the circuits on ball 600, though only a connection to A/D converter 605 is shown. The control logic 616 may be microcontroller, a digital signal processor, or any other processor suitable to the size constraints and functions required to be processed.

To transmit information therefrom, the ball 600 includes an RF oscillator 617. The frequency of the RF oscillator 617 is preferably not the same as the frequency generated by RF oscillator 623 of control unit 620. The RF signal produced by the RF oscillator 617 is modulated with the signal produced by AID converter 605 in an RF modulator 618. The modulated RF signal is amplified by an RF amplifier 619, which is connected to the ball antenna/coil 611. The ball 600 may operate under AM, FM, PM, or any other analog and digital modulation methods. The information transmitted from the ball 600 is received at antenna coil 621 of control unit 620. The RF signal received at antenna/coil 621 is detected by an RF detector 624 and amplified by an RF amplifier 625. The amplified signal is converted to a digital signal by a converter 626, which is an A/D converter or a demodulator. The converter 626 is coupled to control logic 627, which processes the data received from ball 600, and controls a display 628, and other electrical circuitry of control unit 620. The display 628 provides visual signaling to a human operator, and may be as simple as an LED, or as complex as a computer display, or it may simply be an interface to other instrumentation equipment.

Figure 7:
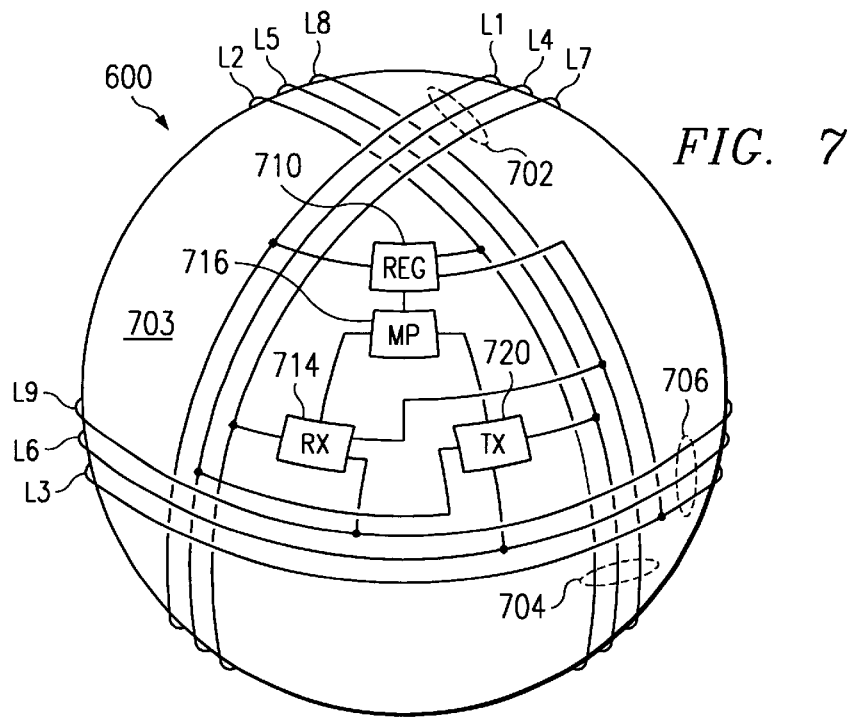
FIG. 7 illustrates spherical geometry of the ball having three sets of coil antennas for improved communication, according to a disclosed embodiment.

Referring now to FIG. 7, there is illustrated the spherical geometry of the ball 600 having three sets of coil antennas for improved communication, according to a disclosed embodiment. The ball 600 (similar to balls 510 and 120) is fabricated on a substantially spherical substrate 703, and includes nine coils $L_1$–$L_9$ in three sets 702, 704, and 706 of three coils, each set 702, 704, and 706 preferably orthogonal to each other so that power and signal communication requirements can be optimized according to the orientation of each ball 600 in the particular procedure. Each coil set 702, 704, and 706 comprises three coils; one transmit coil, one receive coil, and a power coupling coil. Therefore, in this embodiment, there are three power coils $L_1$, $L_2$, and $L_3$; three transmit coils $L_4$, $L_5$, and $L_6$; and three receive coils $L_7$, $L_8$, and $L_9$. The coils sets 702, 704, and 706 are grouped in this fashion to ensure that at least one coil set 702, 704, or 706 is orientated to provide potentially optimum power coupling and signal communication therewith.

Onboard circuitry comprises a processor circuit 716 (similar to control logic 616) for controlling all aspects of the ball 600. The processor circuit 716 can be a digital signal processor or other conventional processors. Power for the ball 600 is provided via a regulator circuit 710 (similar to voltage regulator 614) which regulates power coupled into any of the power coils $L_1$, $L_2$, and $L_3$. Communication is provided by a transmit circuit 720 and a receive circuit 714 (similar to the functions provided by the RF circuits 617, 618, and 619 of FIG. 6). The transmit circuit 720 connects to the three transmit coils $L_4$, $L_5$, and $L_6$ in order to provide transmit communications which are capable of outputting signals in any orientation of the ball 600, and only one of which is included in one of the three sets of coils 702, 704, and 706. Similarly, the receive circuit 714 connects to each of the receive coils $L_7$, $L_8$, and $L_9$, in order to provide receive communications which are capable of receiving signals in any orientation of the ball 600, and only one of which is included in each one of the three sets of coils 702, 704, and 706. The coils $L_1$-$L_9$ can have any number of windings (not shown) in order to achieve the desired results.

The coils $L_1$-$L_9$ are connected by subsurface conductors (not shown) to the other circuit elements on the ball 600. The processor 716 provides an output to the transmitter 720 that preferably radiates an RF signal to the external antenna/coil 621 for processing by the control logic 627 of the control unit 620. The power regulator 710 provides a relatively constant DC voltage of about 3.0 volts to the circuits on the ball 600. A disclosed power source for the ball 600 is provided by the control logic 627 in conjunction with the antenna/coil 621 which couples power to the power coils $L_1$, $L_2$, and $L_3$ in the form of a varying magnetic field. Alternatively, the ball 600 can be powered by a miniature battery connected to the ball 600 (which is discussed in greater detail hereinbelow). The miniature battery can also be in the shape of a ball (battery ball) configured to accommodate a common connection scheme for use between adjacent balls. Preferably, battery balls can be fashioned as electrical double-layer condensers from such materials as manganese dioxide, lithium or lithium ion, samarium-cobalt, carbon, etc. Since such a battery ball is a greater capacity energy source than an RF energy receiving coil, longer communication distances can be achieved by this means. Both the external magnetic field generator (part of which is the control logic 627) and receiver antenna/coil 621 can be included in the same computer-controlled apparatus or CPU station within proximity of the ball 600, at least, but not limited to periods when its operation is required.

Figure 8:
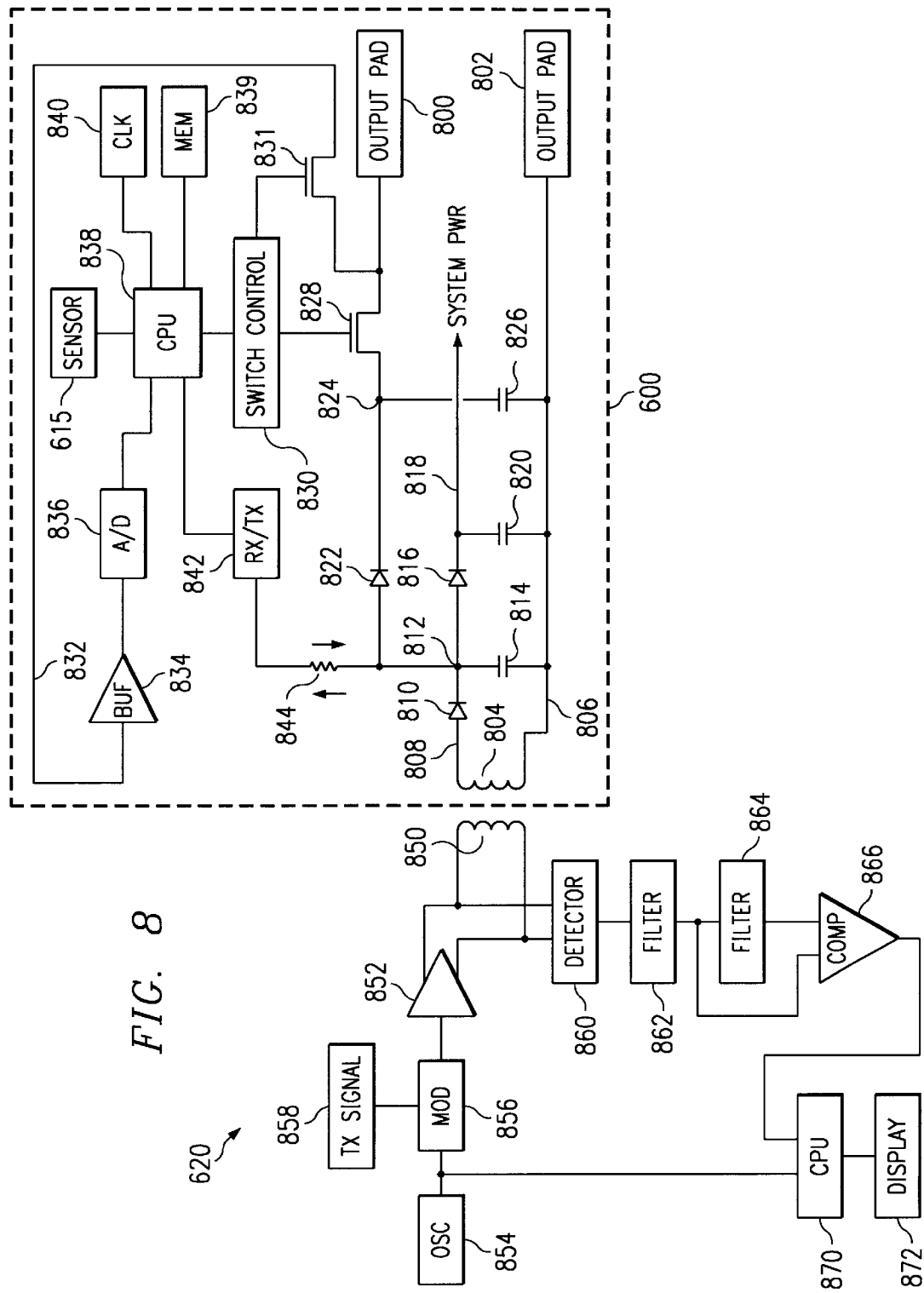
FIG. 8 illustrates a schematic block diagram of the ball having a stimulus capability and the control unit for the powering/detection operation.

Referring now to FIG. 8, there is illustrated a schematic block diagram of the ball 600 having a stimulus capability and the control unit 620 for the powering/detection operation. The ball 600 is operable to provide two electrode contact interfaces, an output pad 800 as an anode and an output pad 802 as a cathode, for interfacing with the desired medium. The spacing between these two pads or contacts 800 and 802 is approximately 0.5 cm. The illustrated embodiment is that associated with a "passive" system, which term refers to the fact that there is no battery associated therewith. In order to operate the system, there is provided an inductive coupling element 804 in the form of an inductor, which is operable to pick up an alternating wave or impulse via inductive coupling and extract the energy therein for storage in the inductive element 804. This will create a voltage across the inductive element 804 between a terminal 806 and a terminal 808. A diode 810 is connected between the node 808 and a node 812, with the anode of diode 810 connected to node 808 and the cathode of diode 810 connected to a node 812. Typically, the diode 810 will be fabricated as a Schottky diode, but can be a simple PN semiconductor diode. For the purposes of this embodiment, the PN diode will be described, although it should be understood that a Schottky diode could easily be fabricated to replace this diode. The reason for utilizing a Schottky diode is that the Schottky diode has a lower voltage drop in the forward conducting direction.

The diode 810 is operable to rectify the voltage across the inductive element 804 onto the node 812, which has a capacitor 814 disposed between node 812 and node 806. Node 812 is also connected through a diode 816 having the anode thereof connected to node 812 and the cathode thereof connected to a node 818 to charge up a capacitor 820 disposed between node 818 and 806. The capacitor 820 is the power supply capacitor for providing power to the ball 600. The capacitor 814, as will be described hereinbelow, is operable to be discharged during operation of the system and, therefore, a separate capacitor, the capacitor 820, is required for storing power to power the ball 600.

The node 812 is connected to the anode of a diode 822, the cathode thereof connected to a node 824. A main capacitor 826 is connected between node 824 and node 806. The capacitor 826, as will be described hereinbelow, is operable to provide the primary discharge energy to the desired medium via the output pad 800, the anode of the ball 600. This node 824 is connected to one side of the gate/source path of a drive transistor 828, the other side thereof connected to the output pad 800. The gate of drive transistor 828 is connected to the output of a switch control circuit 830. Drive transistor 828 is operable to be turned on for a short period of time to connect to the top plate of capacitor 826 to the output pad 800 and subsequently, to conduct current to the desired medium.

In addition to transmitting energy out on output pad 800, there is also provided a sense transistor 831 which has one side of the gate/source path thereof connected to the output pad 800 and the other side thereof connected to a node 832. The gate of sense transistor 831 is connected to the output of the switch control 830. Node 832 is connected to the input of a buffer 834 to generate an analog signal output thereof which is then converted with an A/D converter 836 to a digital value for input to a CPU 838. The CPU 838 is operable to receive and process this digital input voltage. A clock circuit 840 is provided for providing timing to the system. A memory 839 is provided in communication with the CPU 838 to allow the CPU 838 to store data therein for later transmittal back to the remote location or for even storing received instructions. This memory 839 can be volatile or it can be nonvolatile, such as a ROM. For the volatile configuration, of course, this will lose all information when the power is removed. The CPU also connects to the one or more sensors 615 which can be provided on the ball 600 with the stimulus function of the electrodes 606.

The CPU 838 is operable to provide control signals to the switch control 830 for turning on the drive transistor 828 or the sense transistor 831 at the appropriate time. Typically, the drive transistor 828 is controlled to turn on for a period of approximately 0.5 microseconds 60–80 times per minute. Once drive transistor 828 is turned off, then sense transistor 831 can be turned on. Alternatively, sense transistor 831 could be a pass-through circuit such that the CPU 838 can always monitor the voltage on the output pad 800. However, it is desirable with the sense transistor 831 and the sensing operation to sense depolarization in the desired medium after an output voltage has been provided thereto for a short duration of time. The output pad 802 provides the return path of the stimulus current.

In order to communicate with the CPU 838 for transferring data thereto and for allowing the CPU 838 to transfer data therefrom, a receive/transmit circuit 842 is provided for interfacing to node 812 to a resistive element 844. This allows RF energy to be transmitted to node 812. It is important to note that the semiconductor junction across diode 810 is a capacitive junction. Therefore, this will allow coupling from node 812 to node 804. Although not illustrated, this could actually be a tuned circuit, by selecting the value of the capacitance inherent in the design of the diode 810. In any event, this allows an RF connection to be provided across diode 810 while allowing sufficient energy to be input across conductive element 804 to provide a voltage thereacross for rectification by the diode 810 and capacitor 814. Typically, the operating frequency of this connection will be in the MHz range, depending upon the design of which a variety are possible. For example, some of these are illustrated in Beigel, U.S. Pat. No. 4,333,072, entitled "Identification Device, " issued Jun. 1, 1982, and Mogi et. al., U.S. Pat. No. 3,944,982, entitled "Remote Control System For Electric Apparatus, " issued Mar. 16, 1976, which are hereby incorporated by reference. With these types of systems, power can continually be provided to the node 812 and subsequently to capacitors 820 and 826 to allow power to be constantly applied to the electrode output pads 800 and 802. The diode 822 may not be required in order to provide the sufficient charge to capacitor 826, but some type of isolation is required between the capacitor 826 and the capacitor 820. Voltage regulation may also be required in order to provide a shaped pulse on the output pad 800. This could be provided by the switch control 830.

The remote control system 620 which is disposed external to the body and proximate to the one or more balls 600 used in medical procedure, include an inductive element 850 which is operable to be disposed in an area proximate to the skin, exterior to the body, and in the proximity of the ball 600. The inductive element 850 is driven by a driving circuit 852 which provides a differential output that is driven by an oscillator 854. This will be at a predetermined frequency and power level necessary to couple energy from inductive element 850 to inductive element 804. Since this control system 620 is external to the body, the power of the oscillator 854 can be set to a level to account for any losses through the body tissues. To allow information to be transmitted, a modulation circuit 856 is provided which is modulated by a transmitter signal in a block 858 that allows information to be modulated onto the oscillator signal 854, which oscillator 854 provides a "carrier" signal. However, it should be understood that the information that is transmitted to the ball 600 could merely be date information whereas the CPU 838 could operate independent of the information being transmitted to provide the correct timing and waveshape for the output pulses. Alternatively, the entire control of the system may be provided by the transmit signal 858 and the information carried thereon, because power must be delivered to the illustrated embodiment when there is a lack of an independent power source in the ball 600. In the present disclosure, the information transmitted to the ball 600 is frequency selective or it is ID dependent. In the frequency selective mode, the transmit signal 858 operates at a select frequency for a particular ball when multiple balls 600 are imbedded. Each ball 600 will be tuned to its associated frequency. This can be for both power and command information. In the ID mode, each ball 600 has a particular ID associated therewith and stored in memory 839, and will only create the stimulus when its ID is transmitted by the transmitter 858. In this mode, all balls 600 are powered at the same time. Additionally, the power levels can be reduced, such that a separate transmit circuit can be provided for each ball 600 and disposed on the skin proximate to the associated ball 600 with the central control system 620 controlling the plurality of separate transmit circuits.

The information received from the ball 600 is modulated upon the oscillator signal driving the inductive element 850. This information is extracted therefrom via a detector 860 which has the output thereof input to a first low pass filter 862 and then to a second low pass filter 864. The output of low pass filters 862 and 864 are compared with a comparator 866 to provide the data. The filter 862 will provide an average voltage output, whereas the filter 864 will provide the actual digital voltage output. The output of the comparator 866 is then input to a CPU 870 which also is powered by the oscillator 854 to process the data received therefrom. This data can then be input to a display 872 for presentation to the operator of the control system 620.

Figure 9A:
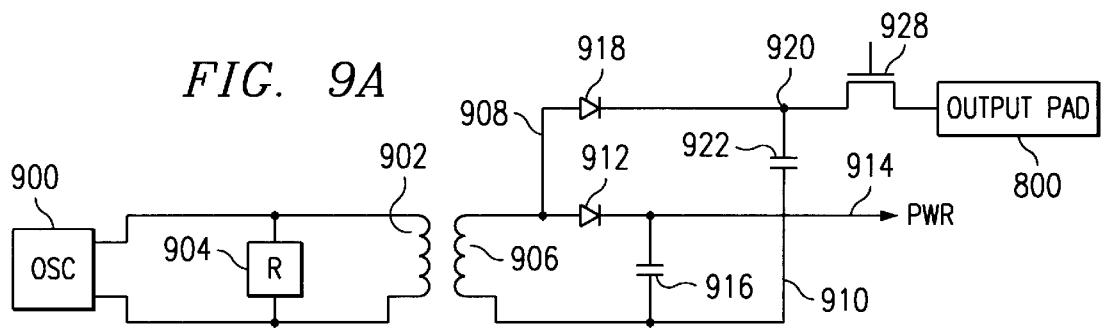
FIG. 9A illustrates an oscillator which drives an external inductive element which may be utilized to couple both electrical power and information or data.
Figure 9B:
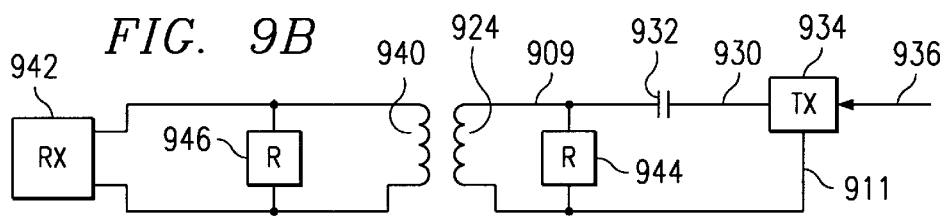
FIG. 9B illustrates a receive operation which utilizes a separate inductive element or antenna in the ball.
Figure 9C:
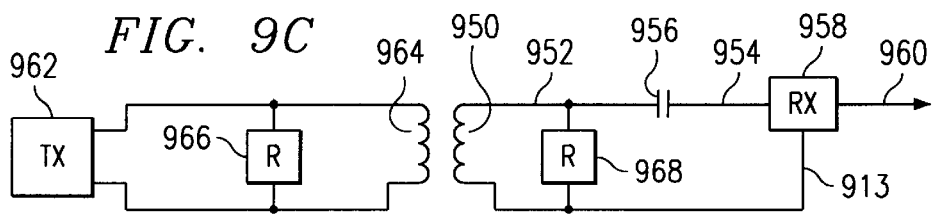
FIG. 9C illustrates a simplified schematic diagram of the transmit embodiment.

Referring now to FIGS. 9A–C, there are illustrated alternate embodiments for the transmit/receive operation of ball 600 when functioning as an stimulator. In FIG. 9A, there is provided an oscillator 900 which drives an external inductive element 902 which may be utilized to couple both electrical power and information or data. Typically, there is some type of load 904 disposed across the inductive element 902. A separate inductive element 906 (similar to inductive element 804), inductively coupled to inductive element 902, is provided on the ball 600. Voltage generated across the inductive element 906, and connected between a node 908 and a node 910, is applied across rectifier 912, which is connected between node 908 and a power node 914. A power supply capacitor 916 disposed across node 914 and node 910 stores the rectified voltage for use by the circuit. Similarly, a rectifier 918 is connected between the node 908 and a node 920 which is connected to one side of a main "surge" capacitor 922. The other side of capacitor 922 is connected to node 910. This capacitor 922 is similar to the main "surge" capacitor 826 in FIG. 8. The switch transistor 928 is provided for connecting the node 920 to the output pad 800.

Referring now to FIG. 9B, there is illustrated a receive operation which utilizes a separate inductive element or antenna 924 in the ball 600, and which is operable to be connected between nodes 909 and 911. Node 909 is capacitively coupled to a transmit node 930 with a capacitor 932, the capacitor 932 being a coupling capacitor. A transmitter 934 is provided for transmitting received data from a line 936 to the node 930 which is then coupled to the node 909 to impress the RF signal across the inductive element 924.

A corresponding inductive element 940 is disposed on the external remote controller, which inductive element 940 is operable to be disposed proximate to the inductive element 924 for inductive coupling therewith, but external to the body having the ball 600 implanted therein. The inductive element 940 operates as a "pick-up" element to receive information, i.e., to function as an antenna, providing the received signal to a receiver 942. The structure of FIG. 9B is a separate structure, such that node 909 is isolated from node 908, the power receiving node illustrated in FIG. 9A. However, it should be understood that harmonics of the oscillator 900 may be coupled into the inductive element 924. These harmonics may be tuned out by using a tuning element 944 on the ball 600 disposed across inductive element 924, and also a tuning element 946 disposed across the inductive element 940, i.e., the antenna.

Referring now to FIG. 9C, there is illustrated a simplified schematic diagram of the transmit embodiment. The ball 600 has associated therewith a separate receive antenna, shown as an inductive element 950, disposed between a node 910 and a node 952. Node 952 is capacitively coupled to a receive node 954 with a coupling capacitor 956. A receiver 958 is provide for receiving the information transmitted thereto and providing on the output thereof data on a data line 960. The receiver 958 is operable to receive the RF signal, demodulate the data therefrom, and provide digital data on the output 960. External to the human body having the ball 600 implanted therein is a transmitter 962 which is operable to impress a signal across an external inductive element 964. The inductive element 964, tuned with a tuning element 966, basically provides for coupling the RF energy with inductive element 950. A corresponding tuning element 968 is provided on the ball 600 and disposed across inductive element 950. The inductive element 950 and the inductive element 964, one being inside the body and the other being external to the body, function as the antennae for coupling RF signal energy across the interface between the ball 600 and the control system 620.

Referring now to FIG. 10, there is illustrated a cross-sectional view of the semiconductor device in the form of the spherical IC which has been "planarized" to remove the curvature thereof for discussion purposes herein. A semiconductor substrate 1000 has disposed thereon various integrated circuits. In general, the semiconductor structure represents an exemplary implementation of the main capacitor 826, the diode 822 and the transistor 828 illustrated in FIG. 8. During fabrication, multiple layers of conductive material are disposed on the substrate separated by insulating oxide layers. These can be polycrystalline silicon layers or they can be metal layers.

The first step in the process is to form the active areas. A first active area is defined for forming the transistor 1028. This transistor 1028 is formed by first defining an active area 1004 and then depositing a thin layer of gate oxide thereover by conventional techniques. A gate electrode 1006 is then formed by depositing a layer of polycrystalline silicon on the substrate, patterning and etching the substrate to define the gate electrode 1006 separated from the surface of the silicon by a gate oxide layer. The edges of the gate electrode 1006 are then utilized to form source/drain implants 1008 on either side thereof . Disposed therebetween is a channel region. Similarly, during the processing in a P-type substrate, wherein the source/drain implants 1008 are N-type substrate material, an N-type implant region 1010 is formed followed by the formation of a P-implant region 1012 therein with an N-type contact region 1014 disposed within the region 1012. The region 1012 and the region 1014 essentially form a PN diode, the diode 1018. Once the active devices have been fabricated, another layer of polycrystalline silicon is disposed onto the substrate and etched to form various layers. One structure is a lower capacitor plate 1019, over which is deposited a layer of oxide 1020. This is the capacitor dielectric oxide layer. This layer of oxide 1020 may be deposited as thin a layer as permitted by the process technology without resulting in a significant amount of defects which might destroy the quality of the resulting capacitor.

After this structure 1019 is formed, typically from a second layer of polycrystalline silicon or even from the first layer of polycrystalline silicon that was utilized to form the gate electrode 1006, a subsequent process step will form a metal layer 1024 thereover. As is well known, capacitance varies inversely with the thickness of the dielectric. Thus, the effective area of the capacitor and the thickness of the dielectric and the type of material utilized as the dielectric will define the capacitor value. Typically, a dielectric layer thickness of between 300 Å to 500Å can be deposited for the gate oxide. Various techniques can provide a silicon dioxide deposition on the order of 100 Å. However, the thinner the capacitor dielectric layer, the more susceptible a large area capacitor is to processing problems which may result in a large number of defects in the capacitor. These are typically manifest as small conductive "shorts" between the layer 1024 and the structure 1019.

Prior to the formation of the structure 1024, vias 1026 and 1027 are formed through oxide layer 1020 previously deposited to expose a portion of the N-region 1014 and also a portion of a contact structure 1030 that is the conductive layer contacting the source/drain region 1008 of the transistor 1028. The vias 1026 and 1027 are then filled with a conductive plug of polycrystalline silicon or metal to provide a conductive connection between one side of the upper capacitor plate formed from the structure 1024 to the diode 1018 and the transistor 1004. The other side of the transistor 1028, the source/drain region 1008, is connected to an opposite side contact 1036 which will connect to the output pad 800.

With the structure of FIG. 10, there is provided a capacitor in series with a diode. Although not illustrated, the structure 1018, comprising the lower plate of the capacitor, is connected to the ground node which constitutes the output pad 802 of FIG. 8. The area of this structure 1018 must be substantially the same as that of the upper structure 1024, the effective area being that of the overlap between the two structures. The plate structures comprise a very large portion of the surface of the spherical IC to provide a sufficient amount of capacitance. For the present application of a pacemaker, the capacitor must store enough energy to deliver approximately 25 micro joules of energy to the surrounding myocardium. This can be accomplished by increasing the area of the capacitor, decreasing the thickness of the capacitor dielectric or increasing the voltage across the capacitor (the stored energy being directly proportional to the square of the voltage).

Referring now to FIG. 11, there is illustrated a cross-sectional diagram of the surface of the ball 600 illustrating conductive strips 1110 which form the inductive element 804. The conductive strips 1110 are spaced above the surface of the integrated circuit of the ball 600 by a predetermined distance, and separated therefrom by a layer of silicon dioxide. A passivation layer 1111 is then disposed over the upper surface of the conductive strips 1110. The conductive strips 1110 can be fabricated from polycrystalline silicon but, it would be preferable to form them from the upper metal layer to result in a higher conductivity strip. This will allow the strips 1110 to be narrower and separated from each other by a larger distance. This separation would reduce the amount of capacitance therebetween.

One end of the strips 1110 is connected to a diode structure 1113. The diode structure 1113 is formed of an N-well implant region 1114 into which a P-well implant region 1116 is disposed, and an N-well implant region 1118 disposed within the P-well implant region 1116. This forms a PN diode where one end of the conductive strips 1110, a conductive connection 1120, is connected to the P-well 1116 implant region, and a conductive layer 1122 is connected at one end to the N-well implant region 1118. This conductive layer or strip 1122 extends outward to other circuitry on the integrated circuit and can actually form the capacitor. Since it needs to go to a capacitor directly, a lower plate 1124 formed of a layer of polycrystalline silicon or metal in a double-metal process, could be provided separated therefrom by a layer of oxide.

In another application, the ball 600 ball functions as a TENS (Transcutaneous Electrical Nerve Stimulator) unit. This is very important in treating chronic pain syndromes. The unit can also be used to stimulate both nerve and muscles in paralyzed or injured limbs to help prevent the development of atrophy or as a means to reduce the inflammatory response. Multiple balls 600 which function as both receivers of electrical signal and also as transmitters of signal could function as a bridge between an amputated limb and a moveable prosthetic "hand."

Referring now to FIG. 12, there is illustrated a perspective view of the ball 600, wherein the inductive element 804 is illustrated as being strips of conductive material wrapped around the exterior of the ball 600. The inductive element 804 is formed of a conductive strip wrapped many times around the ball 600. The length of inductive element 804 depends upon the receive characteristics that are required. As described hereinabove with reference to FIGS. 9A–C, there could be multiple conductive strips, each associated with a receive function, a transmit function or a power function, or they could all share one single conductive element or strip. On one end of the ball 600 there is provided a stimulator interface 1200 of the electrodes 606 having, optionally, one or more interface contacts 1202 (or nodules) associated therewith extending from the sensor interface surface to provide enhanced engagement of the measuring surface or physical entity. The interface contacts 1202 can be made of non-reactive material, e.g., gold to prevent degradation while in the body. Note that in some applications, the interface nodules 1202 are not required for obtaining the desired quantitative data. On the other end of the ball 600 are provided interconnect balls 1204 (or nodules) for interconnecting to one or more other spherical balls 600 which may provide similar functions such as monitoring of quantitative data, or unique functions such as supplying only power or data buffering and storage.

Figure 13:
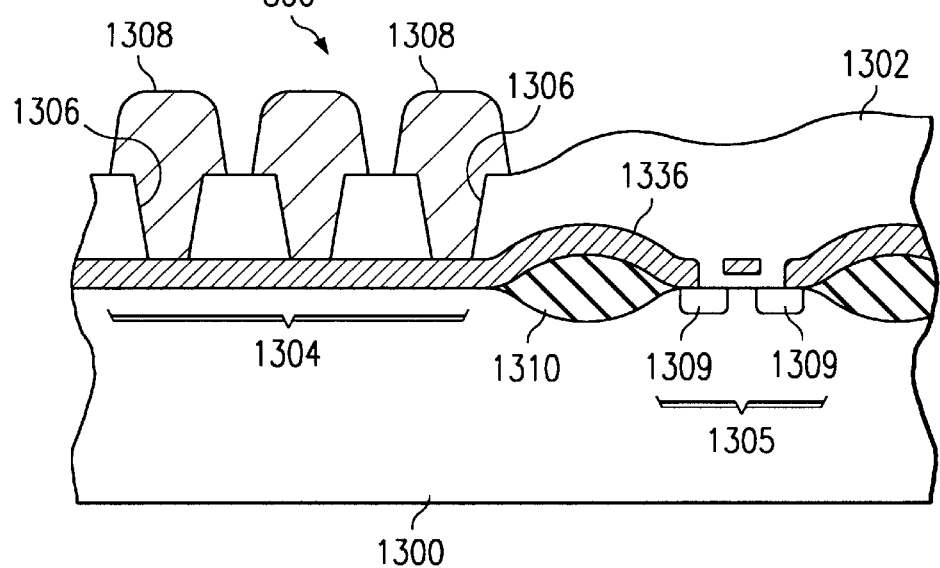
FIG. 13 illustrates a cross-sectional view of the output pad of FIG. 8.

Referring now to FIG. 13, there is illustrated a cross-sectional view of the output pad 800 of FIG. 8. In general, the output pad 800 is required to provide a conductive interface between the transistor 828 and the desired medium. This therefore requires some type of metallic interface that is non-reactive. Such an interface would require a metal such as gold, platinum and the like. In the disclosed embodiment, gold would be provided. After the formation of the upper metal layer 1336 over a substrate 1300 via a deposition technique with metal such as aluminum or copper, a passivation layer of oxide 1302 is deposited to basically prevent oxidation of the metal layer 1336, and protect the semiconductor circuits, in general. The metal contact layer 1336 extends beyond the active region 1305 to an output pad region 1304, and is separated from the active region 1305 by a layer of field oxide 1310 or some type of isolation oxide.

There may be some type of channel stop implant disposed below the field oxide layer 1310. The metal contact layer 1336 extends from the source/drain implant 1309 to the output pad region 1304. This metal contact layer 1336 is required to be fairly conductive. Typically, polycrystalline silicon is not of sufficient conductivity to meet this requirement. Therefore, some type of polysilicide process will be required, wherein the upper surface is converted to some type of silicide such as titanium disilicide to lower the surface resistivity thereof. Alternatively, a metal layer could be provided which is connected to the metal contact region 1336.

Once the contact region 1336 is formed, and the passivation layer 1302 is disposed over the entire structure, vias 1306 are formed therein. These vias 1306 are then filled with metallic plugs 1308 by forming a layer of metal over the oxide passivation layer 1302 and then etching the passivation layer 1302 to remove the undesired portions. The metal plugs 1308 may be formed of metal such as aluminum or gold. If they were formed of gold, this would allow for soldering if they were to be used as contacts. However, in this context, these plugs 1308 are utilized for conductivity purposes. Therefore, an aluminum plug would be sufficient if it were covered with a thin layer of gold to render the aluminum non-reactive and prevent oxidation thereof. Alternatively, in the disclosed embodiment, the plug may, of course, be gold. However, it should be understood that any type of non-reactive metal could be utilized as long as the surface thereof is sufficiently non-reactive and the conductance of the plug 1308 is sufficiently high to result in a low resistance path between the exterior of the spherical ball 600 and a capacitive plate of the capacitor 826. The reason for this is that the stored charge must be discharged into a resistance as low as 500 Ohms, and any significant resistance disposed between the upper plate of the capacitor 826 and the exterior must be minimized.

Figure 14:
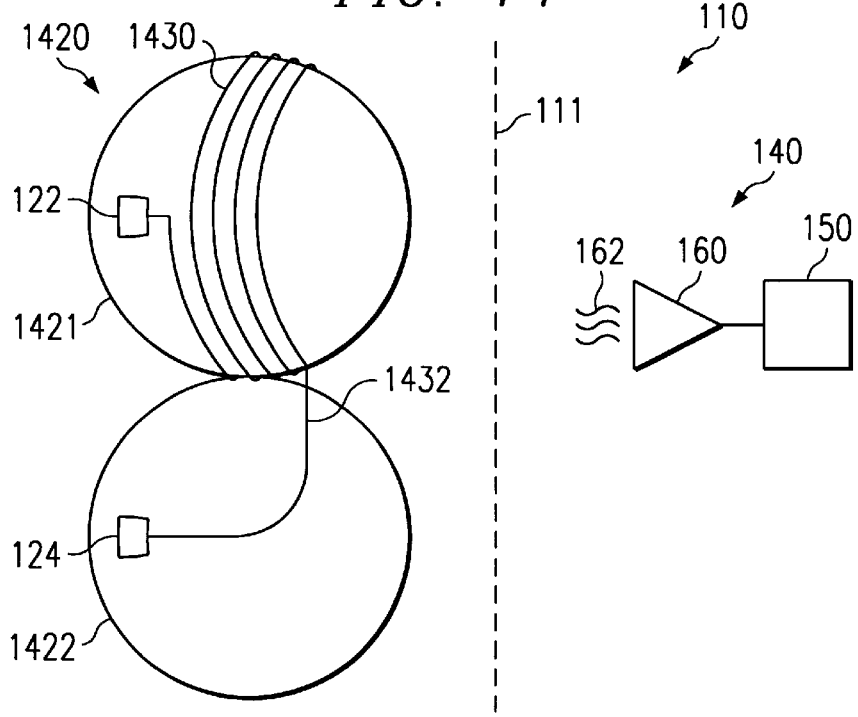
FIG. 14 illustrates an alternative embodiment having first and second ball devices defining an electrode pair.

Referring now to FIG. 14, there is illustrated an alternative embodiment having first and second ball devices defining an electrode pair 1420. A first ball 1421 includes the antenna 1430 (similar to antenna 130, and antenna/coil 611) having one end connected to the cathode 122. The first ball 1421 is in close proximity, if not contacting the second ball 1422, where the other end of the antenna 1430 contacts the second ball 1421 and terminates at the anode 124. The antenna/coil 1430 is adapted to the electrode pair 1420 for wirelessly receiving the electrical pulses 162 from the remotely located electrical pulse generator 140 of the external control system 110. A coil portion of the antenna/coil 1430 is wound around the first ball 1421, and an electrical connector 1432 is used between the first ball 1421 and the second ball 1422 to complete the electrical path between electrode pair 1420.

The remotely-located electrical pulse generator system 140 comprises a generator 150 for generating the electrical pulses and an antenna 160 (similar to antenna/coil 621) for wirelessly transmitting the generated electrical pulses 162 to the first ball 1420. In this embodiment, first ball 1420 and hence the electrode pair defined by the first ball 1421 and the second ball 1422 of this electrode 1420 are embedded in a mass of nervous system tissue 215 of the brain. Electrical pulses generated and transmitted to the first ball 1420 by the remote electrical pulse generator 140 are picked up by the wireless receiving antenna 1430 defined on the ball 1421 and applied to said electrode 1420 to cause the mass of nervous system tissue 215 of the brain located between the cathode 122 and anode 124 to become stimulated to therapy a pathological condition.

In both embodiments, the distance between any anode and cathode pair defines the gap across which electrical pulses received by the ball 600 are transmitted. The amount of nervous tissue mass between these electrodes defines the amount of nervous tissue mass that may be stimulated by electrical pulses using this invention. In the embodiment in FIG. 1, for example, both anode 124 and cathode 122 are located on the same ball 120, and so necessarily, the distance between electrodes, and hence the amount of nervous system tissue between the electrodes that can be excited is small. In contrast, the embodiment of FIG. 14 has more distance between any pair of electrodes and hence more nervous system tissue between pair of electrodes that can be stimulated with electrical pulses using this invention.

While the embodiments described hereinabove have been directed to excitation of nervous system tissue in the brain, it will be appreciated that any nervous system tissue in the body, such as in the spinal regions, can be stimulated using this invention. Furthermore, neuro-stimulation is known to be particularly useful in the therapy of pathological conditions such as epilepsy, movement disorder, chronic pain, behavioral disorder, or psychiatric disorder.

Referring now to FIG. 15, there is illustrated an electrode pair 1420 defined by the semiconductor balls having been placed in the mass of nervous tissue 215 of the brain to wirelessly receive electrical pulses generated from a remote location by a electrical pulse generator. The wireless communication by RF eliminating any need for wires, cables, or connecting needles allows the ball circuits to have minimal disruption to normal brain and spinal tissue activity. Placement of the ball electrode pair 1420 in the mass of nervous tissue 215 can be by surgical implantation, injection, by means of an intraluminal catheter, or by other means for attachment and placement. It should be understood that multiple electrode pairs could be implanted in the nervous system tissue 215.

Semiconductor balls of small size such as one millimeter or less in diameter allow for placement of neuro-stimulators of the disclosed embodiments pervasively throughout nervous system tissues for the purpose of stimulating the tissues with electromagnetic energy. The minute size also allows the electrodes to be positioned in the body using minimally invasive techniques. Additionally, energization of the ball semiconductor electrodes from a remote external control unit 140 eliminates the need for an implantable power source or the retrieval or replacement of such an implanted power source for recharging purposes, although such implantable and closely coupled power sources are disclosed hereinbelow.

Referring now to FIG. 16, there is illustrated a side view of an alternate embodiment of a two-ball electrode stimulator 1600 having an onboard power source. The two-ball implementation comprises two ball structures 1602 and 1604, and a power supply generating structure 1608 for storing a power supply voltage.

Diodes must be provided for receiving and rectifying a large amount of power and charging up a power supply capacitor, in addition to a main "surge"capacitor, for providing a relatively large amount of pulsed energy to the desired medium when in the stimulus configuration. The space 1608 between the ball 1602 and the ball 1604 may contain either a battery or a capacitor, represented by a structure 1610. This is disposed between a supporting structure having supporting ends 1612 and 1618 which interface to the ball 1600 and 1602 structures, respectively.

Referring now to FIG. 17, there is illustrated a schematic block diagram of the stimulator of FIG. 16 having an onboard battery 1710 as a power source. The battery 1710 is provided which is connected to a capacitor 1712. The capacitor 1712 could be identical to the capacitor 826 of FIG. 8 in that it could be formed on the surface of the spherical ball 600, or it could actually be part of the battery structure 1610 shown in FIG. 16. The battery 1710 is placed across the capacitor 1712 to provide sufficient charge therefor. Additionally, the capacitance 1712 could actually be the capacitance of the battery 1710. Additional structure could be provided for powering the CPU 838 and the other circuitry on the chip from the battery 1710. As such, there would only be required a smaller inductive element 1714 and the capacitor 1716 to allow the receive/transmit block 842 to receive/transmit information from and to the remote exterior control system 620. The CPU 838 is operable to provide control signals to the switch control 830 for turning on the drive transistor 828 or the sense transistor 831 at the appropriate time. Typically, the drive transistor 828 is controlled to turn on for a period of approximately 0.5 microseconds 60–80 times per minute. Once drive transistor 828 is turned off, then sense transistor 831 can be turned on. Alternatively, sense transistor 831 could be a pass-through circuit such that the CPU 838 can always monitor the voltage on the output pad 800. However, it is desirable with the sense transistor 831 and the sensing operation to sense depolarization in the desired medium after an output voltage has been provided thereto for a short duration of time. The output pad 802 provides the return path of the stimulus current.

Figure 18:
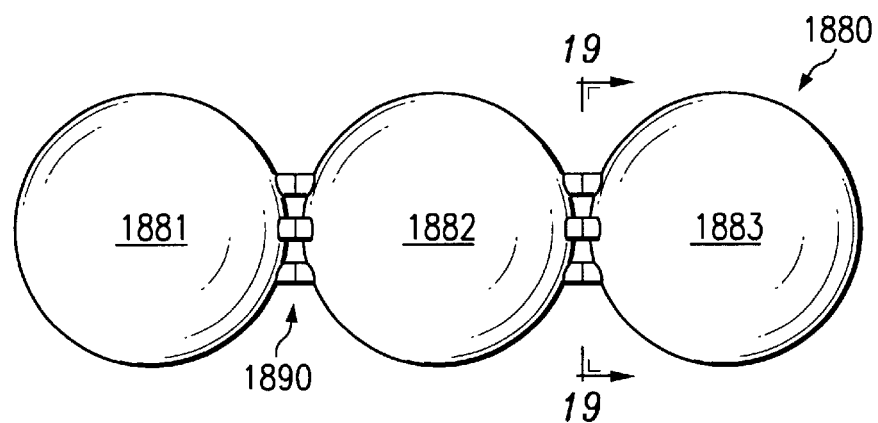
FIG. 18 illustrates a side elevation of a cluster of three semiconductor balls that may be employed in a cooperative function.

Referring now to FIG. 18, there is illustrated a side elevation of a cluster 1880 of three semiconductor balls that may be employed in a cooperative function. Although a single ball can include the foregoing functions, more complex monitoring functions with multiple sensors and simulators can be implemented by using multiple ball systems for tissue stimulation, and for attachment to prosthetics, catheters, needles and other medical-related apparatus. For example, ball 1881 (similar to ball 600) can include power receiving and data transmission functions. Alternatively, ball 1881 can be a miniature ball-shaped battery. The ball 1882 can include a first transducer function, such as pressure and/or temperature sensing, and ball 1883 can include a stimulator function, for exciting tissues or other biological medium, as the particular application requires. Connections between the balls 1881, 1882, and 1883 are made through metal contacts 1890, which may be solder bumps, and as described in greater detail hereinbelow, the metal contacts 1890 may be used for a variety interface functions, such as power, data, and a signal bypass path.

Figure 19:
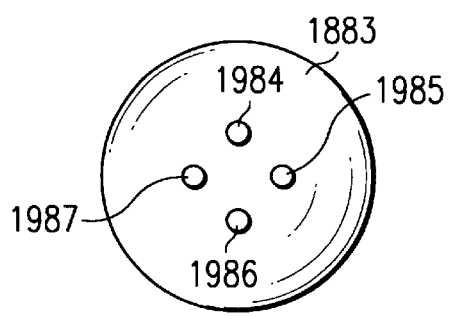
FIG. 19 illustrates a cross section taken along a line 19—19 of FIG. 18.

Referring now to FIG. 19, there is illustrated a cross section taken along a line 19—19 of FIG. 18. As mentioned hereinabove, the contacts 1890 may be employed to interface a variety of functions. For example, the contacts 1984 and 1986 may be power contacts, such as a positive 3.0 volts and ground, which can be passed from ball 1881 (if ball 1881 were to provide the power function for the set 1880) to ball 1882, and then around ball 1882 to ball 1883 by conductors on the surface of ball 1882, using two of a group of similar contacts of contacts 1890 to power ball 1883. The contacts 1985 and 1987 may be data and control contacts for communications between balls of the set 1880. Similar data and control contacts may exist among contact group 1890 between ball 1882 and ball 1883 to the extent needed.

Figure 20:
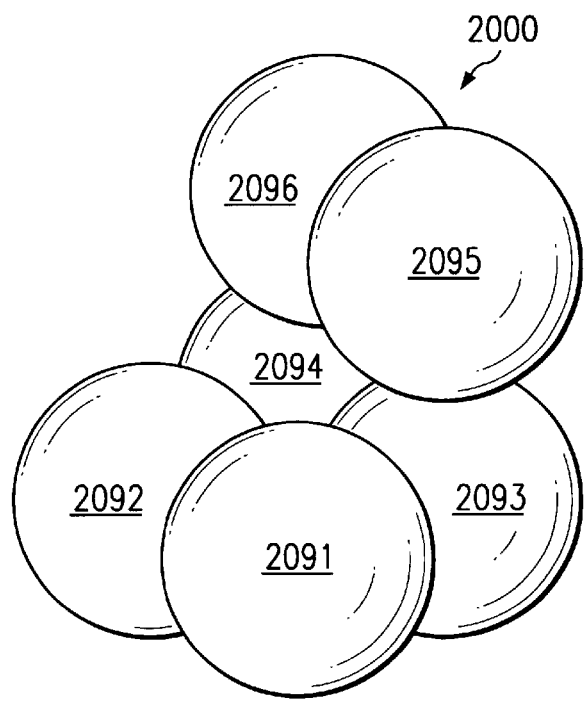
FIG. 20 illustrates a 3-D ball cluster in a cooperative orientation.

Referring now to FIG. 20, there is illustrated a 3-D ball cluster 2000 in a cooperative orientation. As an example of the versatility of such ball systems is illustrated where the cluster 2000 specifically shows six balls 2091, 2092, 2093, 2094, 2095 and 2096 (all similar to ball sensor 600), arranged in a three-dimensional configuration. It will be appreciated that various other cluster arrangements are possible which have fewer balls, and are limited only by the constraints of the end-use application. Each of the balls 2091, 2092, 2093, 2094, 2095 and 2096, of the cluster 2000 can perform different electronic functions, and communicate with each other through contacts (not shown here, but discussed in detail in FIGS. 18 and 19). Such cluster arrangements can provide a mix of, for example, three battery balls 2091, 2092, and 2093, which provide ample power for the remaining energy-consuming balls, according to the functions provided. Such a mix may be necessary where power needs are greater, for example, a heating application needed for tumor ablation, or for more precise heating applications related to cartilage or ligament treatment.

Although the preferred embodiment has been described in detail, it should be understood that various changes, substitutions and alterations can be made therein without departing from the spirit and scope of the invention as defined by the appended claims.

What is claimed is:

1. A system for stimulating a mass of nervous system tissue in a body, comprising:
    one or more semiconductor balls adaptable to be embedded in the mass of nervous system tissue, said ball comprising,
        an electrode having a cathode and an anode; and
        a receiver for wirelessly receiving electrical pulses for application to said electrode; and
    a remote electrical pulse system, said pulse system comprising,
        a generator for generating said electrical pulses; and
        a transmitter for wirelessly transmitting said generated electrical pulses to said receiver of said one or more semiconductor balls;
    wherein said electrical pulses applied to said electrode cause the mass of nervous system tissue to become stimulated to therapy a pathological condition.

2. The system of claim 1, wherein each of said one or more semiconductor balls is uniquely selectable by a respective unique frequency in a frequency mode, and by a unique ID stored therein in an ID mode, wherein in said frequency mode, multiple frequencies are transmitted to cause respective said one or more semiconductor balls to stimulate the mass of nervous system tissue, and in said ID mode, one or more respective IDs are transmitted to cause respective said one or more semiconductor balls to stimulate the mass of nervous system tissue.

3. The system of claim 1, wherein said pathological condition is epilepsy.

4. The system of claim 1, wherein said pathological condition is a movement disorder.

5. The system of claim 1, wherein said pathological condition is a chronic pain.

6. The system of claim 1, wherein said pathological condition is a behavioral disorder.

7. The system of claim 1, wherein said pathological condition is a psychiatric disorder.

8. A method of stimulating a mass of nervous system tissue in a body, comprising the steps of:
    placing one or more semiconductor balls in the mass of nervous tissue, the one or more semiconductor balls each having,
        an electrode containing a cathode and an anode; and
        a receiver for wirelessly receiving electrical pulses for application to the electrode; and
    generating electrical pulses at a remote location for reception by the receiver, the received electrical pulses coupled to the electrode of the one or more semiconductor balls;
    wherein the electrical pulses applied to the electrode cause the mass of nervous system tissue to become stimulated to therapy a pathological condition.

9. The method of claim 8, wherein each of the one or more semiconductor balls in the step of placing is uniquely selectable by a respective unique frequency in a frequency mode, and by a unique ID stored therein in an ID mode, wherein in the frequency mode, multiple frequencies are transmitted to cause respective the one or more semiconductor balls to stimulate the mass of nervous system tissue, and in the ID mode, one or more respective IDs are transmitted to cause respective the one or more semiconductor balls to stimulate the mass of nervous system tissue.

10. The method of claim 8, wherein the pathological condition is epilepsy.

11. The method of claim 8, wherein the pathological condition is a movement disorder.

12. The method of claim 8, wherein the pathological condition is a chronic pain.

13. The method of claim 8, wherein the pathological condition is a behavioral disorder.

14. The method of claim 8, wherein the pathological condition is a psychiatric disorder.

15. The method of claim 8, wherein the step of placing the ball in the mass of nervous tissue includes the step of surgically implanting the electrode in the mass of nervous tissue.

16. The method of claim 8, wherein the step of placing the ball in the mass of nervous tissue includes the step of injecting the ball into the mass of nervous tissue.

17. The method of claim 8, wherein the step of placing the ball in the mass of nervous tissue includes the step of delivering the ball to the site of the mass of nervous tissue by means of an intraluminal catheter.

18. The method of claim 8, wherein the ball is approximately one millimeter in diameter.

19. The method of claim 18, wherein the ball is encapsulated in a substantially biologically inert coating.

20. A ball semiconductor system for stimulating a mass of nervous system tissue in a body, comprising:
    a first semiconductor ball comprising a cathode and a second semiconductor ball comprising an anode, said first and second semiconductor balls forming an electrode pair, said electrode pair adaptable to be embedded in the mass of nervous system tissue;
    a receiver adapted to said electrode pair for wirelessly receiving electrical pulses having application to said electrode pair; and
    a remote electrical pulse system, comprising,
        a generator for generating said electrical pulses;
        a transmitter for wirelessly transmitting said generated electrical pulses to said receiver adapted to said electrode pair;
    wherein said electrical pulses applied to said electrode pair cause the mass of nervous system tissue to become stimulated to therapy a pathological condition.

21. The system of claim 20, wherein each of said electrode pairs is uniquely selectable by a respective unique frequency in a frequency mode, and by a unique ID stored therein in an ID mode, wherein in said frequency mode, multiple frequencies are transmitted to cause respective said electrode pairs to stimulate the mass of nervous system tissue, and in said ID mode, one or more respective IDs are transmitted to cause respective said electrode pairs to stimulate the mass of nervous system tissue.

22. The system of claim 20, wherein said pathological condition is epilepsy.

23. The system of claim 20, wherein said pathological condition is a movement disorder.

24. The system of claim 20, wherein said pathological condition is a chronic pain.

25. The system of claim 20, wherein said pathological condition is a behavioral disorder.

26. The system of claim 20, wherein said pathological condition is a psychiatric disorder.

27. A method of stimulating a mass of nervous system tissue in a body for therapeutic purposes, comprising the steps of:

forming a cathode on a first semiconductor ball, and an anode on a second semiconductor ball, the first and second semiconductor balls forming an electrode pair;

interconnecting the anode and the cathode with a receiver for wirelessly receiving electrical pulses having application to the electrode pair;

implanting the first and second semiconductor balls into the mass of nervous tissue; and generating electrical pulses at a remote location and wirelessly transmitting the generated electrical pulses to the receiver of the electrode pair;

wherein the electrical pulses received by the receiver energize the electrode pair causing the mass of nervous system tissue to become stimulated to therapy a pathological condition.

28. The method of claim 27, wherein each of the electrode pairs in the step of forming is uniquely selectable by a respective unique frequency in a frequency mode, and by a unique ID stored therein in an ID mode, wherein in said frequency mode, multiple frequencies are transmitted to cause respective electrode pairs to stimulate the mass of nervous system tissue, and in the ID mode, one or more respective IDs are transmitted to cause respective the electrode pairs to stimulate the mass of nervous system tissue.

29. The method of claim 27, wherein the pathological condition is epilepsy.

30. The method of claim 27, wherein the pathological condition is a movement disorder.

31. The method of claim 27, wherein the pathological condition is a chronic pain.

32. The method of claim 27, wherein the pathological condition is a behavioral disorder.

33. The method of claim 27, wherein the pathological condition is a psychiatric disorder.

34. The method of claim 27, wherein the step of placing the semiconductor balls in the mass of nervous tissue includes the step of surgically implanting the semiconductor balls in the mass of nervous tissue.

35. The method of claim 27, wherein the step of placing the semiconductor balls in the mass of nervous tissue includes the step of injecting the semiconductor balls in the mass of nervous tissue.

36. The method of claim 27, wherein the step of placing the semiconductor balls in the mass of nervous tissue includes the step of delivering the semiconductor balls to the site of the mass of nervous tissue by means of an intraluminal catheter.

37. The method of claim 27, wherein the semiconductor balls are approximately one millimeter in diameter each.

38. The method of claim 27, wherein each semiconductor ball is encapsulated in a substantially biologically inert coating.

* * * * *